United States Patent [19]

Tatom

[11] Patent Number: 4,773,398

[45] Date of Patent: Sep. 27, 1988

[54] PHYSICAL THERAPY APPARATUS

[76] Inventor: Andrew J. Tatom, 2019 Tate Springs Rd., Lynchburg, Va. 24501

[21] Appl. No.: 797,976

[22] Filed: Nov. 14, 1985

[51] Int. Cl.[4] .......... A61L 1/02

[52] U.S. Cl. .......... 128/25 R; 272/143

[58] Field of Search .......... 128/25 R, 25 B, 77, 128/80 R, 26; 272/93, 117, 132, 143, 129, 67, 68, 125; 73/379

[56] References Cited

U.S. PATENT DOCUMENTS

| | | | |
|---|---|---|---|
| 2,777,439 | 1/1957 | Tuttle | 128/25 R |
| 3,618,595 | 11/1971 | Stahmer et al. | 128/25 R |
| 4,333,340 | 6/1982 | Elmeskog | 73/379 |
| 4,407,496 | 10/1983 | Johnson | 272/117 |
| 4,592,545 | 6/1986 | Sagedahl et al. | 272/125 |
| 4,603,856 | 8/1986 | Fiore | 272/143 |

FOREIGN PATENT DOCUMENTS

| | | | |
|---|---|---|---|
| 0923543 | 5/1982 | U.S.S.R. | 128/25 R |

OTHER PUBLICATIONS

Cybex II Handbook, pp. 3 and 32-45, 1981.

*Primary Examiner*—Richard J. Apley
*Assistant Examiner*—J. Welsh
*Attorney, Agent, or Firm*—Daniel E. McConnell

[57] ABSTRACT

A physical therapy apparatus for enabling proprioceptive neuromuscular facilitation of a multi-axis body structure and having a shaft which rotates in controlled movement about an axis and a body engaging component for engaging an extremity of a patient's limb and which is coupled with said shaft for controlled movement of the component with the shaft through an arc of a circle while accommodating rotation of the component about an axis perpendicular to said shaft and translation of the component along an axis parallel to said shaft, the apparatus accomplishing movement of the patient's limb through a predetermined angular range.

7 Claims, 3 Drawing Sheets

PHYSICAL THERAPY APPARATUS

FIELD AND BACKGROUND OF INVENTION

This invention relates to a physical therapy apparatus and particularly to an apparatus for enabling proprioceptive neuromuscular facilitation of a patient's body structure. Therapeutic exercise apparatus typical of those known prior to this invention are shown in prior U.S. Pat. Nos. 2,777,439 to Tuttle; 3,089,700 to Hotas; 4,258,913 to Brentham; 4,355,633 to Heilbrun; and 4,407,496 to Johnson.

The value of proprioceptive neuromuscular facilitation in the rehabilitation of persons suffering from various disabilities has been recognized in the relevant literature and significant effort has been devoted to developing procedures for such therapeutic exercise. Less attention has been devoted to the development of apparatus which enables such exercise, particularly with regard to the complex movements of which the human body is capable. One difficulty which can be and has been encountered in connection with the design and development of apparatus intended for such therapeutic exercise is the relative ease of developing apparatus capable of accomodating movement around a single axis, and the great difficulty in applying such apparatus in exercising body structure capable of multi-axis movement.

Specific examples of such apparatus and body structure are the apparatus known by the trademark "Cybex" and the human shoulder joint. The Cybex apparatus is a well recognized and widely used apparatus which is quite successfully applied in therapeutic exercise of joints and muscle structure which either inherently are or are adaptable to single axis function, such as an elbow or ankle. The shoulder joint should be capable of an exceptional freedom of movement, sometimes called global, which rarely has a single axis of motion and often has axes which move as the movement proceeds. Particularly where disability affects performance of normal movement, therapeutic exercise desirably should be able to involve movement of the body structure in such a manner.

BRIEF STATEMENT OF INVENTION

With the foregoing comments in mind, it is an object of the present invention to provide an apparatus which is capable of accomplishing movement of a body portion undergoing therapeutic exercise through a predetermined angular range while accomodating multiple and shifting axes of such movement. In realizing this object of the present invention, possibilities are opened for effective therapeutic exercise of such body portions as a shoulder joint.

A further object of this invention is to accomplish the accomodation of therapeutic exercise which involves movement of a body portion through an arc of a circle while also through rotation and translation. In realizing this object of the present invention, body engaging means for engaging an extremity of a patient's limb is coupled to a means for rotating a shaft in controlled movement about an axis, such as a single axis exercise apparatus, by a linkage arrangement which is capable of rotation about and translation along an axis having particular relationships to the axis of rotation of the shaft.

BRIEF DESCRIPTION OF DRAWINGS

Some of the objects of the invention having been stated, other objects will appear as the description proceeds, when taken in connection with the accompanying drawings, in which.

DETAILED DESCRIPTION OF INVENTION

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

Figure 2:
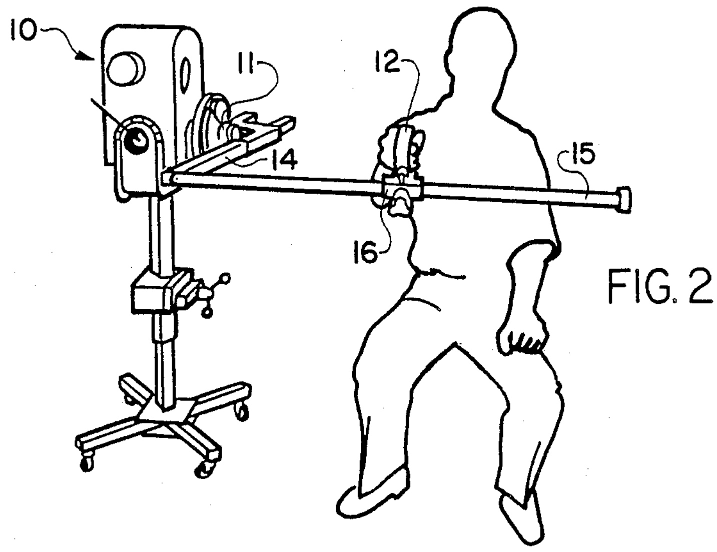
FIG. 2 is a perspective view of the apparatus of FIG. 1 in a second operating position.
Figure 1:
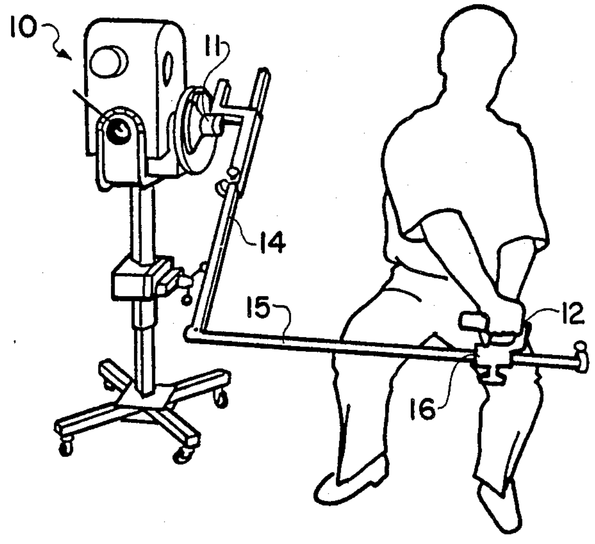
FIG. 1 is a perspective view of an apparatus of the present invention in a first operating position.
Figure 3:
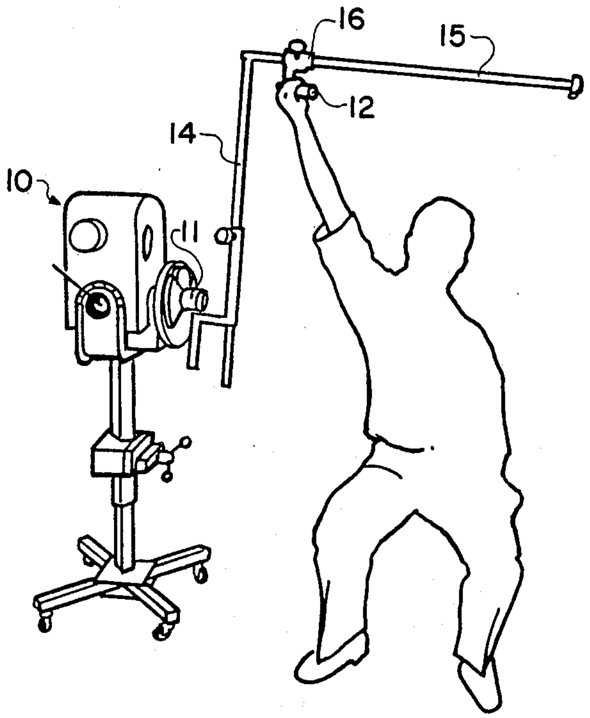
FIG. 3 is a perspective view of the apparatus of FIGS. 1 and 2 in a third operating position.

Referring now more particularly to the drawings, the sequence of views shown in FIGS. 1 through 3 illustrates the use of apparatus in accordance with this invention in connection with therapeutic exercise of a patient's shoulder. As there illustrated, and as will be noted from a comparison of the views, the apparatus is used in manipulation of the shoulder joint of a patient. In such manipulation, the patient's arm is moved in a manner similar to that of a radial member describing an arc of a circle, while the hand and wrist rotate and the hand moves sideways or across the major vertical axis of the patient's body. With such manipulation, a substantial portion of the global range of movement of the arm and shoulder are achieved.

The apparatus as illustrated in FIGS. 1 through 3 includes a means (indicated at 10) for rotating a shaft (indicated at 11) in controlled movement about an axis. In preferred forms of this invention, the means 10 takes the form of known therapeutic exercise apparatus such as the Cybex machine available from the Cybex Division of Lumex, Inc. of Ronkonkoma, N.Y. Such apparatus, in accordance with this invention, is provided with appropriate means such as adapters and the like to accomodate the attachment of accessory components as will be described more fully hereinafter.

In order to accomplish cooperation with the limb of a patient, the apparatus according to this invention has means for engaging the extremity of a patient's limb, and particularly the extremity of the limb undergoing therapeutic exercise. In the form illustrated, as as preferred for this invention, the means takes the form of a handle 12 which is gripped by a patient during use of the apparatus. The handle 12 moves with the patient's hand and thus the extremity of the arm in particular paths as described hereinabove and hereinafter.

The handle 12 is coupled to the shaft 11 by means which accomplish controlled movement of the handle with the shaft and through an arc of a circle while accomodating rotation of the handle about an axis perpendicular to the shaft and translation of the handle along an axis parallel to the shaft so as to move the patient's arm through a predetermined angular range. The coupling means comprises a first arm 14 which is fixed to the shaft for rotation therewith and which extends perpendicularly to the axis of rotation of the shaft. Preferably, the first arm 14 (FIG. 4) is of some material such as a square rod which may be readily engaged by and with adapters mounted on the shaft 11, and is drilled with a plurality of holes spaced along the rod to accomodate engagement by a locking pin so as to permit adjustment of the spacing of the handle 12 from the patient's shoulder and thereby accomodate patients of varying size.

Figures 4, 5, 6:
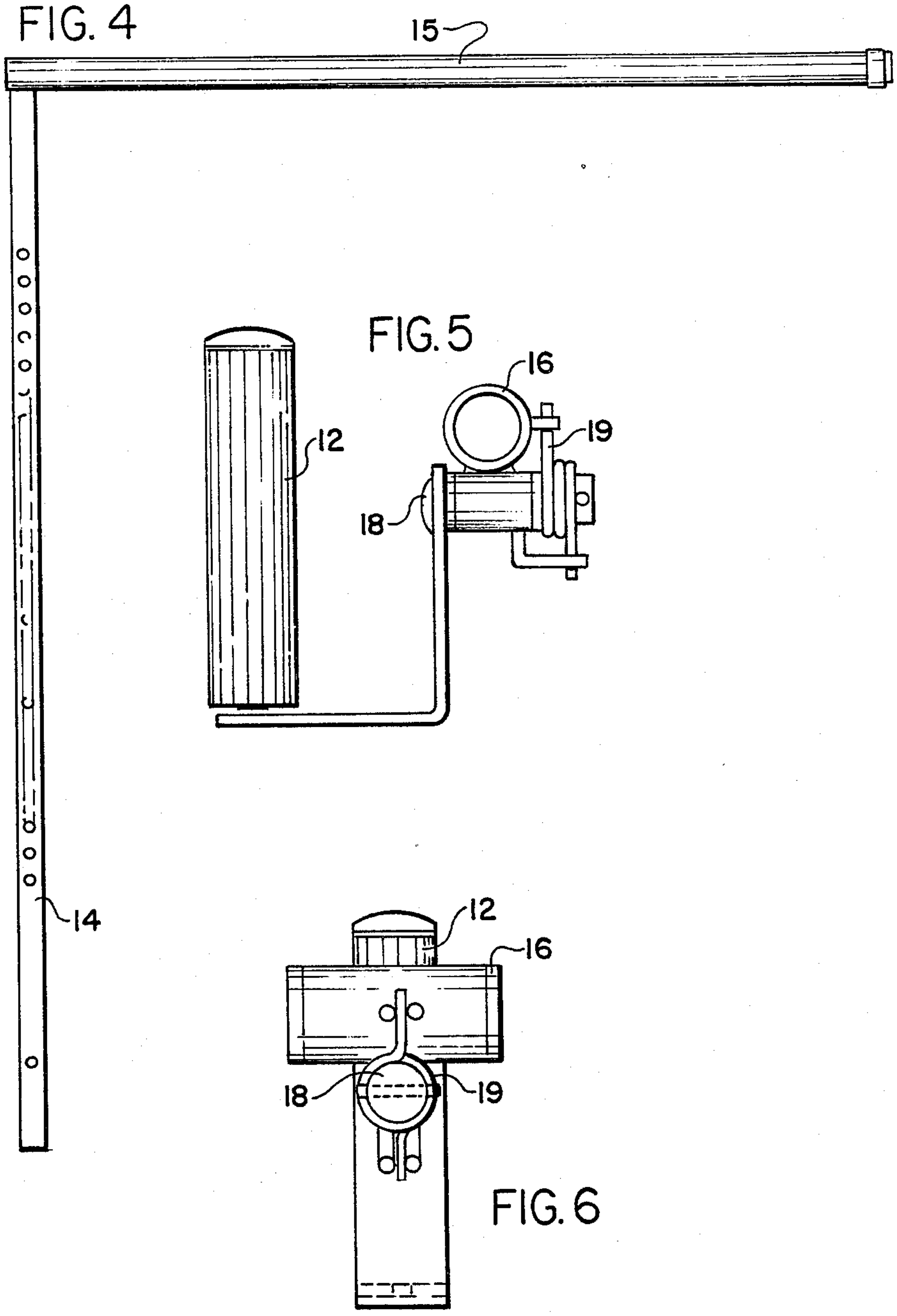
FIG. 4 is an elevation view of a portion of the apparatus of FIGS. 1 through 3, showing in greater detail certain attachment features of such portions.
FIG. 5 is an enlarged elevation view from the side of a portion of the apparatus of FIG. 4.
FIG. 6 is a plan view of the apparatus of FIG. 5.

At an end of the first arm 14 remote from the location of attachment to the shaft 11 is secured a second arm means indicated at 15 (FIG. 4). The second arm 15 may be welded to the first arm 14 or fastened with a bolted or threaded joint or the like. The second arm functions for defining an axis of translation which is parallel to, and which rotates about, the axis of the shaft 11. By means of the adjustment provided for the first arm, the radius of the arc of a circle described by the second arm may be varied as described above. The second arm preferably is made of a round rod material, and mounts the handle 12 for translation therealong in accomodation of angular motion of a shoulder joint as in apparent by comparison of FIGS. 1 and 3.

Mounting of the handle 12 on the second arm 15 is accomplished by handle structure which includes a sleeve 16 sized to engage the second arm and guide sliding movement of the handle therealong. A friction clamping means incorporated in the handle may permit adjusting the freedom of the handle to slide along the arm. Additionally, the handle structure includes a pivot pin 18 disposed perpendicularly to the second arm 15 and arranged to accomodate rotation of the handle (and thus of the patient's arm) about a swivel axis perpendicular to the axis of rotation of the shaft 11. Means, shown in the form of a spring 19, are provided for establishing a resistance against such rotation as an aid to the therapeutic exercise contemplated by this invention. The resistance means may provide a variable resistance either by way of using a selected spring out of a set or by the provision of an adjustable force spring arrangement.

In use in manipulation of an arm as descibed hereinabove, a patient is seated adjacent the apparatus of this invention in a position generally similar to that illustrated in FIG. 1, and the apparatus is adjusted to the size of the patient. The patient is then instructed to grasp the handle 12, and the drive means 11 is operated to move the patient's arm through a repetitive cycle of movement between positions such as those of FIGS. 1 and 3, or as otherwise selected by a competent medically trained person supervising the therapeutic exercise.

The present invention has been shown and described with particular reference to the shoulder joint of a patient undergoing therapeutic exercise. However, it is contemplated that the apparatus described may be used with any body portion capable of movement of the types described. One further particular example of such a joint is the hip joint, which is, in similarity to the shoulder joint, capable of an exceptional freedom of movement. In such an application, the patient's limb exercised would be the leg and the extremity engaged would be the foot.

In the drawings and specifications there has been set forth a preferred embodiment of the invention and, although specific terms are used, the description thus given uses terminology in a generic and descriptive sense only and not for purposes of limitation.

What is claimed is:

1. The combination of a physical therapy apparatus having means for rotating a shaft in controlled movement about an axis of the apparatus with means for enabling proprioceptive neuromuscular facilitation of a multiaxis body structure and comprising:

first means for coupling with said shaft and defining an axis of translation and rotation parallel to and spaced from the axis of rotation of said shaft, said first means moving with said shaft for describing with said axis of translation and rotation a portion of the surface of a cylinder about said axis of rotation of said shaft, and structurally rigid body engaging means for engaging an extremity of a patient's limb and mounted on said first means (a) for rotation of said body engaging means about an axis perpendicular to said axis of translation and rotation, (b) for translation of said body engaging means along said axis of translation and rotation, and (c) for rotation of said body engaging means about said axis of translation and rotation, said combination moving the patient's limb through a predetermined angular range while the extremity of the limb rotates about said perpendicular axis and translates along said axis of translation and rotation to describe a spiral and to enable proprioceptive neuromuscular facilitation of the associated joint by exercising the limb.

2. The combination according to claim 1 wherein said means for coupling said body engaging means with said shaft comprises a first arm means fixed to said shaft for rotation therewith and extending perpendicularly to the axis of rotation of said shaft and a second arm means mounted on said first arm means for rotation therewith about said axis of shaft rotation and for defining an axis of translation for said body engaging means extending parallel to said axis of shaft rotation, said first and second arm means being connected with said shaft for adjustment of the radius from said axis of shaft rotation at which said axis of translation moves in describing said arc of a circle.

3. The combination according to claim 2 wherein said body engaging means is mounted on said second arm means for rotation about an axis perpendicular to both said axis of translation and said axis of shaft rotation.

4. The combination according to claim 2 wherein said body engaging means is mounted on said second arm means for rotation about an axis perpendicular to said axis of translation and for translation along said axis of translation.

5. The combination according to claim 4 wherein said body engaging means comprises means for imposing a predetermined resistance to rotation of said body engaging means about said axis perpendicular to said axis of translation and rotation.

6. The combination of a physical therapy apparatus having means for rotating a shaft in controlled movement about an axis of the apparatus with means for enabling proprioceptive neuromuscular facilitation of a multiaxis body structure such as a shoulder and comprising:

first means for coupling with said shaft and defining an axis of translation and rotation parallel to and spaced from the axis of rotation of said shaft, said first means moving with said shaft for describing with said axis of translation and rotation a portion of the surface of a cylinder about said axis of rotation of said shaft, and structurally rigid body engaging means for engaging a patient's hand and mounted on said first means (a) for rotation of said body engaging means about an axis perpendicular to said axis of translation and rotation, (b) for translation of said body engaging means along said axis of translation and rotation, and (c) for rotation of said body engaging means about said axis of translation and rotation, said rotation and translation of said body engaging means occurring because of restraints imposed by the function of the patient's arm, and said combination moving the patient's arm through a predetermined angular range while the patient's hand rotates about said perpendicular axis and translates along said axis of translation and rotation to describe a spiral and to enable proprioceptive neuromuscular facilitation of the shoulder by exercising the arm.

7. A method of providing proprioceptive neuromuscular facilitation for a multi-axis joint associated with an elongate limb of a patient and comprising the steps of coupling the extremity of a patient's limb to a structurally rigid body engaging means, then driving the body engaging means to move through space along a path on a portion of the surface of a cylinder described about the axis of rotation of a driving shaft, while rotating the extremity about the longitudinal axis of the limb, and translating the extremity along an axis parallel to and spaced from the axis of rotation of the driving shaft, and rotating the body engaging means about the axis along which the extremity is translated, the rotating and translating occurring because of restraints imposed by the function of the patient's limb, so that the patient's limb is moved through a predetermined angular range while the extremity of the limb rotates and translates to describe a spiral and to enable proprioceptive neuromuscular facilitation of the associated joint by exercising the limb.

* * * * *